United States Patent [19]

Lentz et al.

[11] Patent Number: 4,850,980
[45] Date of Patent: Jul. 25, 1989

[54] I.V. PUMP CASSETTE

[75] Inventors: David Lentz, Poway; Victor L. Bartholomew, Escondido, both of Calif.

[73] Assignee: Fisher Scientific Company, Pittsburgh, Pa.

[21] Appl. No.: 129,005

[22] Filed: Dec. 4, 1987

[51] Int. Cl.[4] .............................................. A61M 5/00
[52] U.S. Cl. ................................. 604/248; 604/249; 137/625.17
[58] Field of Search ............... 604/152, 246, 248, 249, 604/32, 33, 151; 128/DIG. 12; 137/625.17, 625.47

[56] References Cited

U.S. PATENT DOCUMENTS

| | | | |
|---|---|---|---|
| 2,547,254 | 4/1951 | Braithwaite | 137/625.17 |
| 3,269,412 | 8/1966 | Badke | 137/625.17 |
| 3,354,910 | 11/1967 | Moen | 137/625.17 |
| 3,985,133 | 10/1976 | Jenkins et al. | 128/214 F |
| 4,047,527 | 9/1977 | Kelsen | 128/229 |
| 4,396,385 | 8/1983 | Kelly et al. | 604/152 |
| 4,423,741 | 1/1984 | Levy | 128/768 |
| 4,450,079 | 5/1984 | Farr | 604/152 |
| 4,604,093 | 8/1986 | Brown et al. | 604/248 |
| 4,605,396 | 8/1986 | Tseo et al. | 604/152 |

Primary Examiner—Stephen C. Pellegrino
Attorney, Agent, or Firm—Nydegger & Harshman

[57] ABSTRACT

A cassette for use with an I.V. infusion pump has a housing with a first inlet, a second inlet, an outlet, and a port to the I.V. infusion pump. A valve body is positioned within the housing to selectively establish fluid communication from the first inlet to the port, or from the second inlet to the port, or from the port to the outlet. Movement of the valve body within the housing into yet another position allows for the free flow of fluid directly between the first inlet or the second inlet and the outlet.

19 Claims, 5 Drawing Sheets

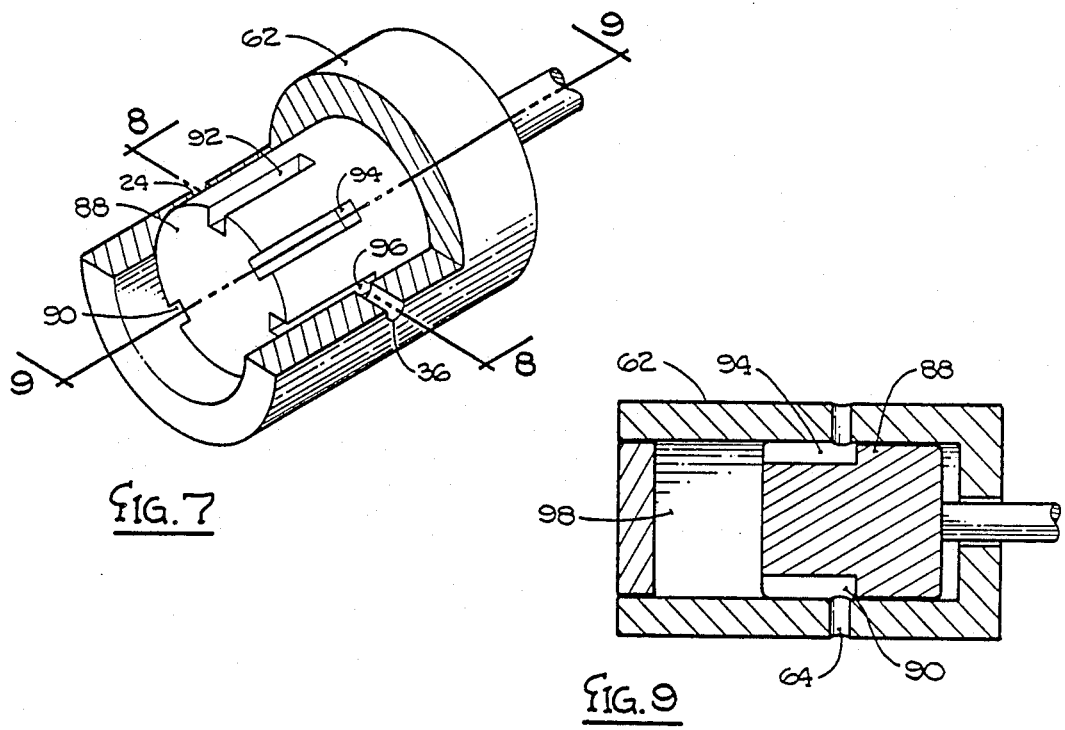
FIG. 7
FIG. 9
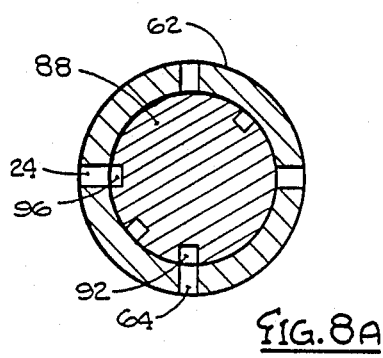
FIG. 8A
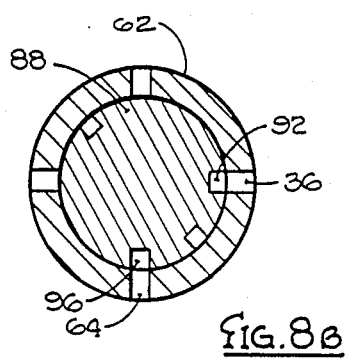
FIG. 8B
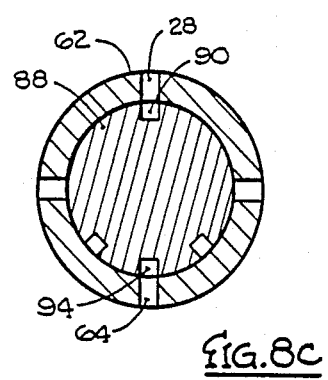
FIG. 8C
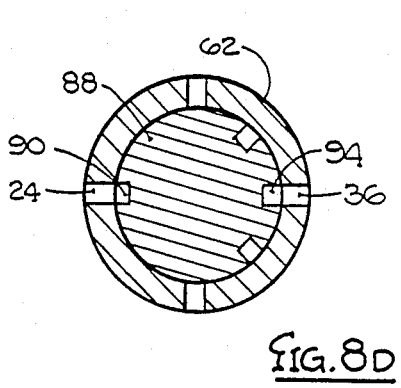
FIG. 8D

I.V. PUMP CASSETTE

BACKGROUND

1. Field of the Invention.

This invention relates generally to disposable pumping chamber cassettes which are used with fluid pumps. The cassette of the present invention is useful for pumps wherein the fluid is to be selectively pumped from either or both of two fluid sources to a patient. This invention is particularly, though not exclusively, useful in conjunction with a pump used for the infusion of I.V. fluids to a patient.

2. Background of the Invention.

The present invention is directed to a pumping chamber for use with a volumetric infusion pump that is particularly adaptable for administering fluids to a patient. When a person is hospitalized, it is often desirable to administer one or more fluids to the patient for either therapeutic or maintenance purposes. Further, it is not uncommon that the concurrent infusion of more than one solution is required.

A common method for introducing medical solutions directly into the patient's bloodstream is by intravenous (I.V.) administration. Under appropriate circumstances, this method affords several advantages. For example, the necessity of giving repeated injections to the patient, and the traumatic response most patients have towards repeated injections, can be eliminated by the use of a standard intravenous (I.V.) procedure. Additionally, precise quantities of the selected solution can be properly administered over protracted periods of time.

An I.V. administration procedure typically requires suspending a container of fluid at an elevated position with respect to the patient. The container is then placed in fluid communication with the patient through a series of tubes and connections which lead to a needle that has been placed into one of the patient's veins. Obviously, the rate of fluid flow and the volume of fluid infused through such a system must be controlled. For this purpose, pumps or controllers can be used in such procedures. Specifically, pumps can be used in I.V. systems for the administration of fluids to a patient when there is a need to provide a mechanical pressure on the fluid being infused.

Volumetric pumps, capable of both fluid volume and flow rate control, typically incorporate a pumping chamber with a valving device which allows the pumping chamber to alternately fill and discharge in accordance with the predetermined rate of fluid flow to the patient. Several examples of these types of I.V. pumps and associated disposal pump chamber cassettes are available. Specifically, U.S. Pat. No. 3,985,133 to Jenkins et al., U.S. Pat. No. 4,423,741 to Levy, and U.S. Pat. No. 4,450,079 to Farr disclose pumps or pump chamber cassettes for an I.V. pumping device.

Further, several valving mechanisms have been suggested for use with pumping chambers. For example, U.S. Pat. No. 3,269,412 to Badke and U.S. Pat. No. 4,423,741 to Levy disclose reciprocating piston valves having various fluid paths defined therein which are oriented with fluid inlets and outlets to a single fluid path through a common chamber. These devices, however, are not able to channel multi-inlet sources to a common pumping chamber and eventually to an outlet. As an added feature, U.S. Pat. No. 4,605,396 to Tseo discloses a pump cassette having the ability to establish a free-flow condition from the inlet to the outlet of the cassette. Again, as with the above-identified references, Tseo does not teach or suggest a cassette with the ability to have two inlet sources feeding a chamber, which subsequently pumps fluid into a patient.

To improve the flexibility of a pumping mechanism in an I.V. infusion system, there is a recognized need for a combination between pumping chamber and valve which provides for the option of using alternate fluid sources either separately or in conjunction with each other. Further, there is a need for such an option without disconnecting the fluid line or interrupting the infusion. With this in mind, it can be appreciated that there is a need for a cassette which can switch to a second fluid source, after a preprogrammed infusion from a first fluid source, and allow fluid from the second source to be pumped through the system. There is also a need for a pump cassette having a chamber for accurately mixing fluid solutions from separate sources at desired concentrations.

The present invention recognizes that the aforementioned needs can be satisfied by a cassette which employs a valve having channels and/or grooves which create passageways by rotational or longitudinal displacement of the valve. Further, the present invention recognizes that this valve in cooperation with a pump cassette will be useful to administer a predetermined quantity of fluids from at least two fluid sources to the patient.

Accordingly, it is an object of the present invention to provide a means for drawing a first medical solution into a chamber, while also having the ability to draw a second medical solution into the same chamber. It is another object of the present invention to provide a pump cassette having means for engaging or disengaging a second I.V. fluid line without interrupting the administration of fluids to the patient from an established I.V. line. Additionally, it is an object of the present invention to provide an inexpensive, easily manufactured and simple to operate device that improves the flexibility of an I.V. administration system.

SUMMARY OF THE INVENTION

The preferred embodiment of the present invention includes a cassette for use with an I.V. infusion pump, which comprises a valve body in operative association with a housing having a first inlet, a second inlet, an outlet, and a port. When the cassette is engaged with the pump, the valve body is operatively engaged with the drive mechanism of the pump for rotation of the valve body in the housing. This engagement between valve and drive mechanism allows the cylindrically shaped valve body to selectively establish fluid communication between the first fluid inlet and the port, or the second fluid inlet and the port, or from the port to the outlet. To accomplish this, the valve body is disposed in the housing of the cassette for rotation therein.

In accordance with the present invention, the valve is also operable through its connection with the pump to establish a free-flow condition directly between the first inlet and the outlet. In an alternate embodiment of the present invention, this free-flow condition can be established when the cassette is disengaged from the pumping mechanism. In this particular alternate embodiment, a button associated with the valve body can be pressed to slidably relocate the valve body in the housing to establish a fluid passageway between the first inlet and the outlet. With all embodiments of the present invention, whenever fluid in the I.V. system can free-flow through the cassette from the inlet to the outlet, the system is easily punged of air.

The novel features of this invention, as well as the invention itself, will be best understood from the accompanying drawings taken together with the accompanying description in which similar reference characters refer to similar parts and which:

BRIEF DESCRIPTION OF THE DRAWINGS

FIG. 7 is a perspective view of an alternate embodiment providing a multi-groove valve in cooperation with the housing of the cassette with portions of the housing broken away for clarity;

FIGS. 8A, B, C and D are end cross-sectional views of a multi-groove valve body in four different configurations in the housing of the cassette as seen along line 8—8 in FIG. 7;

FIG. 9 is a side cross-sectional view of the multi-groove valve body in the housing of the cassette as seen along line 9—9 in FIG. 7;

DETAILED DESCRIPTION OF THE PREFERRED EMBODIMENT

Figures 1, 2:
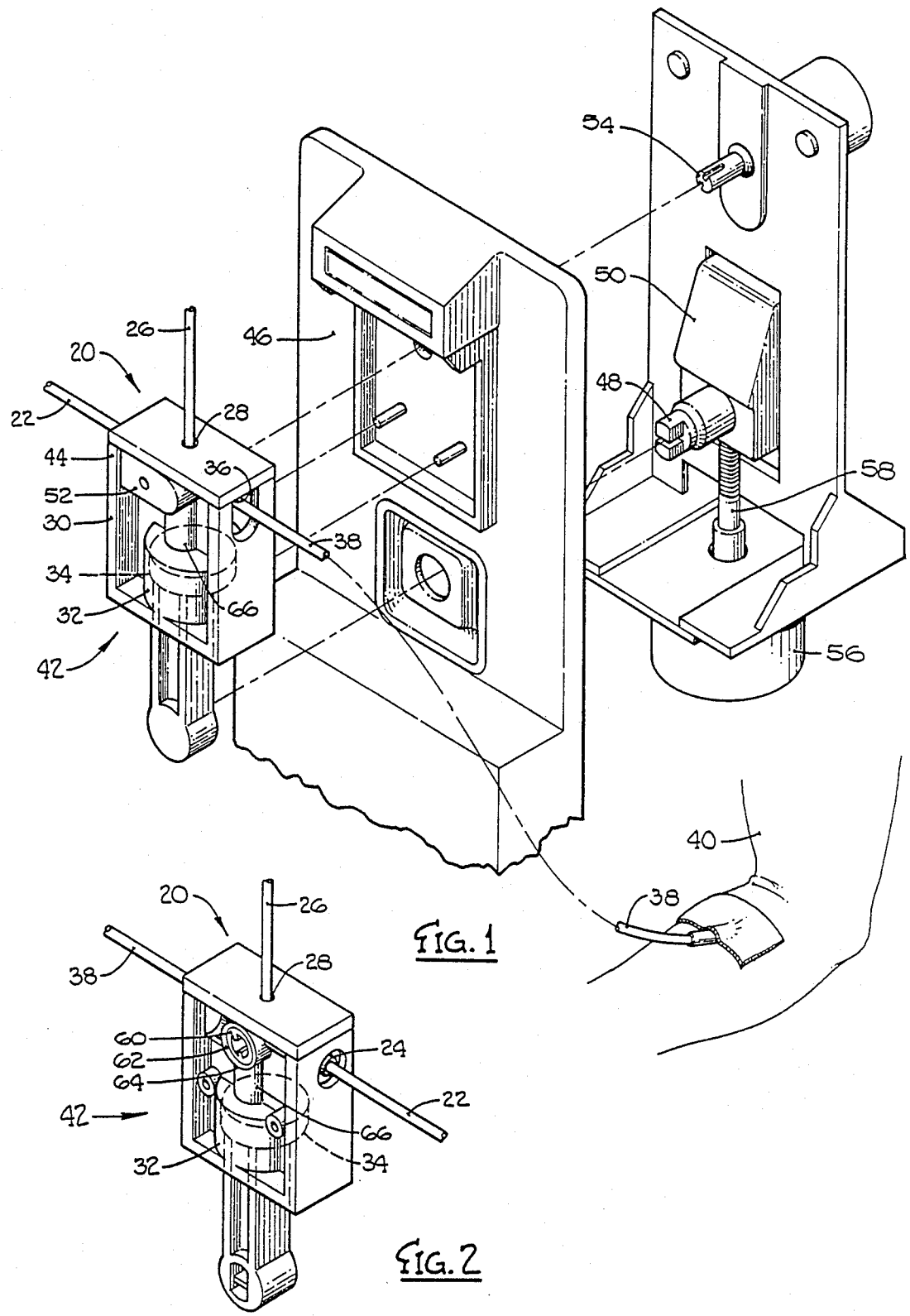
FIG. 1 is a front perspective view of the cassette and its intended association with a pumping mechanism.
FIG. 2 is a back perspective view of the cassette.

Referring now to the drawings, the cassette of the present invention is shown in FIG. 1 and generally designated 20. As seen in FIG. 1, cassette 20 is connectably with a first fluid source (not shown) through a first line 22 which is connected to cassette 20 at a first inlet 24. Cassette 20 is also connectable with a second fluid source (not shown) through a second line 26 which is engaged with cassette 20 at a second inlet 28. Cassette 20 further comprises a casing 30, which is formed with a pump chamber 32. A piston 34 is disposed in pump chamber 32 for reciprocal motion therein to provide a pump action for fluid flowing through cassette 20. As also seen in FIG. 1, an outlet 36 is intended for connection with an outlet line 38, which in turn is connected for the administration of an I.V. solution to patient 40. Still referring to FIG. 1, it is seen that cassette 20 can be associated with a pump, generally designated 42 in FIG. 1. More specifically, the cassette 20 is associated with a pump case 44 in a manner which provides flush engagement between the cassette 20 and a front plate 46.

Engagement of cassette 20 with pump 42 brings a connector 48 into operative contact with a shuttle 50 and also brings a valve mechanism 52 into operative contact with an actuator 54. A stepper motor 56 drives a lead screw 58 which is operatively associated with shuttle 50 to provide for a pumping action of piston 34 within pump chamber 32. Simultaneously with the operation of piston 34, and in cooperation therewith, actuator 54 is driven by pump 42 to operate valve mechanism 52 of cassette 20 to direct fluid from first inlet 24 into pump chamber 32 and subsequently to direct fluid from pump chamber 32 through outlet 36 via outlet line 38 to patient 40. Also, actuator 54 is driven by pump 42 to operate valve mechanism 52 of cassette 20 to direct fluid flow from second inlet 28 into pump chamber 32; and subsequently to direct fluid from pump chamber 32 through outlet 36 and via outlet line 38 to patient 40.

FIG. 2 is a perspective view of cassette 20 and valve mechanism 52 as seen from the back side of cassette 20. In FIG. 2 it can be seen that valve mechanism 52 comprises a valve body 60 seated in a housing 62. In addition to first inlet 24, second inlet 28 and outlet 36, housing 62 is formed with a port 64 which is connected to a pump chamber line 66 that establishes fluid communication between port 64 and pump chamber 32.

Figure 3:
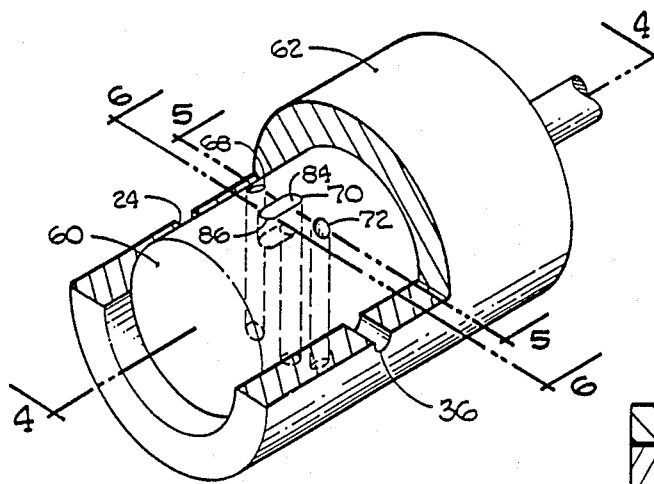
FIG. 3 is a perspective view of an embodiment of the valve in cooperation with the housing of the cassette with portions of the housing broken away for clarity.
Figure 5A:
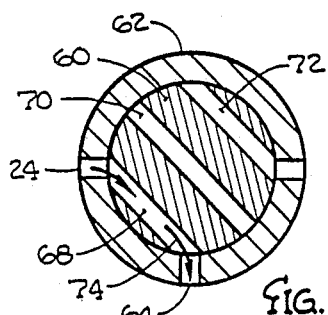
FIGS. 5A, B, C and D are end cross-sectional views of the valve body in the housing of the cassette as seen along the line 5—5 in FIG. 3.
Figure 5B:
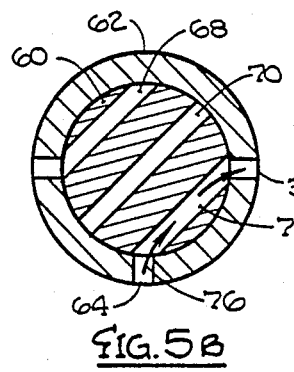

FIG. 3 is a perspective view of one embodiment of valve body 60. As shown, valve 60 is generally cylindrically shaped and has three essentially coplanar parallel passageways. These passageways are, respectively, a first passageway 68, a second passageway 70, and a third passageway 72. Further, as shown in FIG. 3, these passageways are generally oriented perpendicularly to the longitudinal axis of valve 60. As valve 60 is appropriately oriented in housing 62, first passageway 68 allows fluid to flow, as indicated by arrows 74, from first inlet 24 through first passageway 68 to port 64. This configuration is illustrated in FIG. 5A. When valve 60 is oriented in housing 62, as shown in FIG. 5B, the third passageway 72 allows fluid to flow, as indicated by arrows 76, from port 64 through third passageway 72 to outlet 36, and subsequently to the patient 40. With proper alignment of valve 60 in housing 62, second passageway 70 allows fluid to flow, as indicated by arrows 78, from second inlet 28 through second passageway 70 to port 64, as illustrated in FIG. 5D.

As will be best appreciated by reference to FIG. 3, the longitudinal axis of passageways 68, 70 and 72 are coplanar. Passageway 70, however, is formed with a recess 82 at one end which extends along the outer surface of valve 60 in a direction substantially parallel to the longitudinal axis of valve 60. As shown in FIG. 3, recess 82 has a first portion 84 and a second portion 86.

The cooperation of structure for the embodiment of valve 60, shown in FIG. 3, will be best appreciated by considering different elements of structure which are found on two separate parallel planes each of which intersect valve 60 perpendicular to its longitudinal axis. Specifically, these planes are further defined by line 5—5 and line 6—6 in FIGS. 3 and 4. The structural elements of interest in the plane including line 5—5 are:

first inlet 24; port 64; and outlet 36. Also within this same plane are the passageways 68, 70, and 72 and first portion 84 of recess 82. Second portion 86 of recess 82 and second inlet 28 are located in the plane including line 6—6. Accordingly, with valve 60 positioned as shown in FIG. 5A, second passageway 70 and third passageway 72 are blocked by housing 62 and only first passageway 68 is open for fluid communication between first inlet 24 and port 64. With valve 60 positioned as shown in FIG. 5B, first passageway 68 and second passageway 70 are blocked by housing 62. With this orientation, only third passageway 72 is open for fluid connection between port 64 and outlet 36.

Figure 5C:
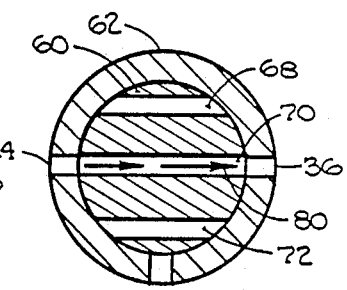
Figure 5D:
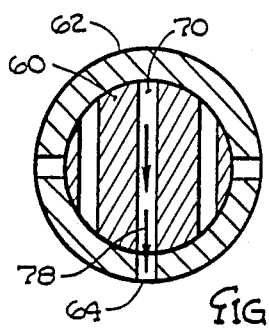

Still considering only those structural elements that lie in the plane which includes line 5—5, it will be seen that with valve 60 oriented as shown in FIG. 5C that passageways 68 and 72 are blocked by housing 62 and that passageway 70 is open for fluid communication, as indicated by arrows 80, between first inlet 24 and outlet 36. Importantly, it is first portion 84 of recess 82 which is aligned with first inlet 24 or outlet 36 whenever fluid communication is established between first inlet 24 and outlet 36. Further, it will be understood that this configuration establishes a free-flow condition from a fluid source (not shown) to outlet 36 which is useful in removing air from the system.

Figure 4:
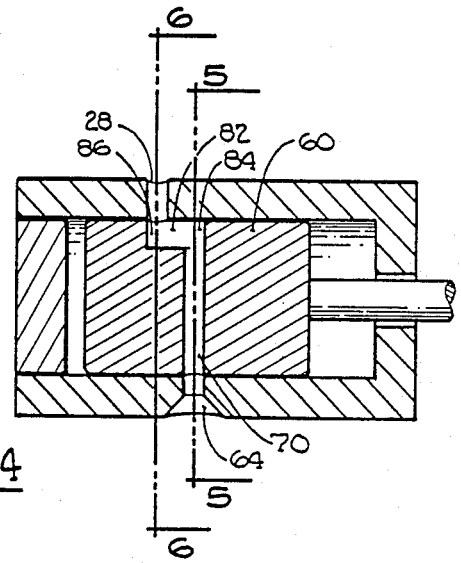
FIG. 4 is a side cross-sectional view of the valve body in the housing of the cassette as seen along line 4—4 in FIG. 3.
Figure 6:
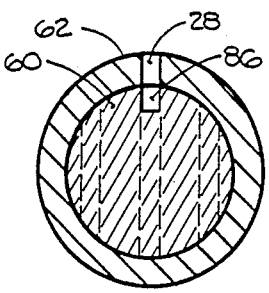
FIG. 6 is an end cross-sectional view of the valve in the housing as seen along the line 6—6 in FIG. 3.

Considering now the elements that lie in the plane which includes line 6—6, it will be seen by referring to FIG. 6 that valve 60 can be oriented in housing 62 to align second portion 86 of recess 82 with second inlet 28. Recognize that this orientation of valve 60 corresponds to the position of valve 60 as shown in FIG. 4. Cross-referencing FIG. 4 and FIG. 5D with FIG. 6, it can be seen that when valve 60 is so oriented there is established a fluid path between second inlet 28 and port 64 which includes recess 82 and second passageway 70. Thus, it is to be understood that second inlet 28 is alignable with second portion 86 of recess 82, but not with first portion 84.

In light of the above, it will be understood by the skilled artisan that valve 60 can be sequentially moved, through connections with pump 42, into appropriate positions, shown in FIGS. 5A, B, C and D, to accomplish the desired fluid flow. Specifically, it will be understood that the purpose and objects of the present invention can be obtained by proper sequential movement of the valve into the various positions disclosed above.

An alternate embodiment of the valve is shown in FIGS. 7, 8A, 8B, 8C, 8D and 9. FIG. 7 is a perspective view of a multiple grooved valve body 88. Specifically, FIG. 7 shows that valve 88 is formed with a series of grooves, 90, 92, 94 and 96 at one end of valve 88. Preferably, grooves 90 and 94 are diametrically opposed and the grooves 92 and 96 are positioned with groove 94 therebetween, as shown. As will be appreciated by reference to FIGS. 8A, B, C and D, that grooves 92 and 96 define an arc on the surface of cylindrically shaped valve 88 which is approximately 90 degrees. FIG. 9 shows that valve 88 is positioned within housing 62 to establish a chamber 98 through which fluid can flow when transiting housing 62 between first inlet 24, second inlet 26, outlet 36 and port 64. Fluid communication between these apertures of housing 62 and chamber 98 is accomplished by proper alignment of valve 88 within housing 62.

With valve 88 oriented as shown in FIG. 8A, fluids can flow from first inlet 24 through groove 96 to chamber 98 and then from chamber 98 through groove 92 to port 64. With valve 88 oriented as shown in FIG. 8B, fluid can flow from port 64 through groove 96 to chamber 98 and then from chamber 98 through groove 92 to outlet 36. When oriented as shown in FIG. 8C, valve 88 allows fluid to flow from second inlet 28 through groove 90 into chamber 98 and then from chamber 98 through groove 94 to port 64. Lastly, valve 88 allows fluid to flow from first inlet 24 through groove 90 into chamber 98 and then from chamber 98 through groove 96 to outlet 36 where it is oriented as shown in FIG. 8D. It will be recognized that FIG. 8D shows a free-flow air purging condition.

Figure 10:
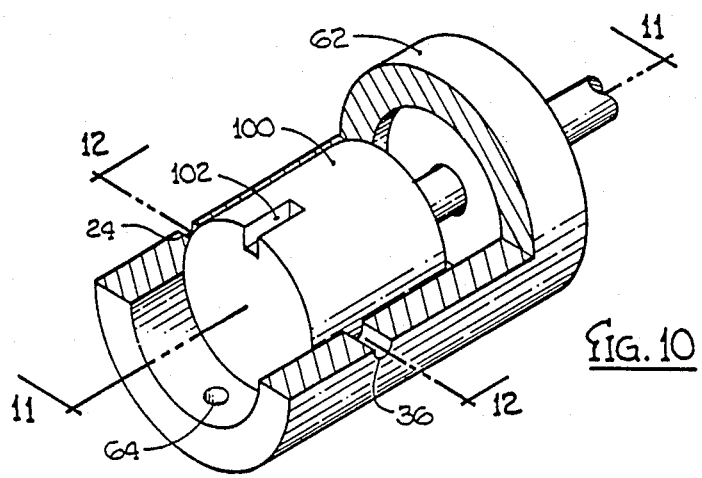
FIG. 10 is a perspective view of another embodiment providing a single groove valve in cooperation with the housing of the cassette with portions of the housing broken away for clarity.
Figure 11A:
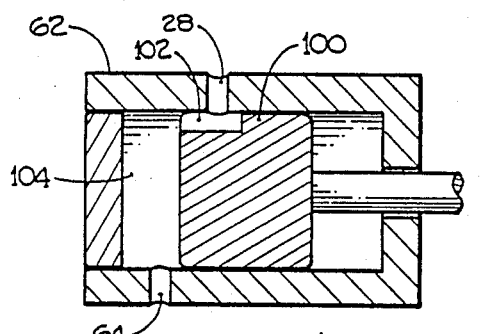
FIGS. 11A and B are side cross-sectional views of the single-groove valve body in the housing respectively in an engaged position and a disengaged position as seen along line 11—11 in FIG. 10.
Figure 12A:
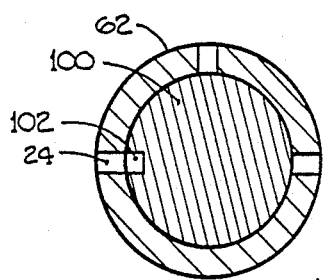
FIGS. 12A, B, C, and D are end cross-sectional views of the single-groove valve body in four different configurations in the housing of the cassette as seen along line 12—12 in FIG. 10.
Figure 12B:
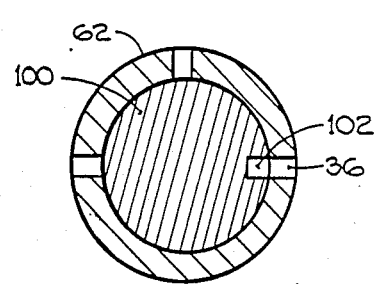
Figure 12C:
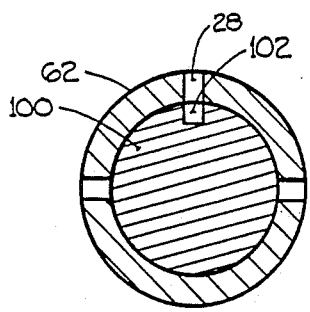
Figure 12D:
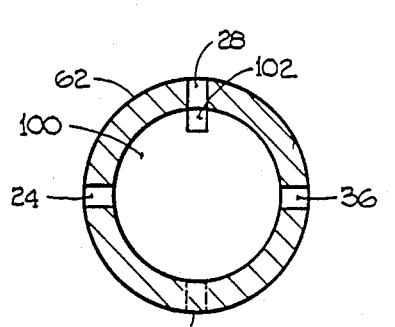

FIG. 10 illustrates still another embodiment of the present invention in which a valve body 100 has a single groove 102. For this embodiment, in addition to being rotatable within housing 62, cylindrically shaped valve 100 is also longitudinally displaceable in housing 62. As seen in FIGS. 11A and B, valve 100 is positioned within housing 62 to create a fluid chamber 104 which is in fluid communication with port 64. Valve 100 when in a first position, as shown in FIG. 11A, is rotatable to selectively establish fluid communication through groove 102 between chamber 104 and first inlet 24, outlet 36 or second inlet 28. These configurations are respectively shown in FIGS. 12A, B and C. More specifically, as illustrated in FIG. 12A, groove 102 allows fluid to flow from first inlet 24 through groove 102 to chamber 104, and subsequently to port 64. Groove 102, when rotated into the position shown in FIG. 12B, allows fluid to flow from port 64 to chamber 104 and through groove 102 to outlet 36. When rotated to the position as shown in FIG. 12C, groove 102 allows fluid to flow from second inlet 28 through chamber 104 to port 64.

Figure 11B:
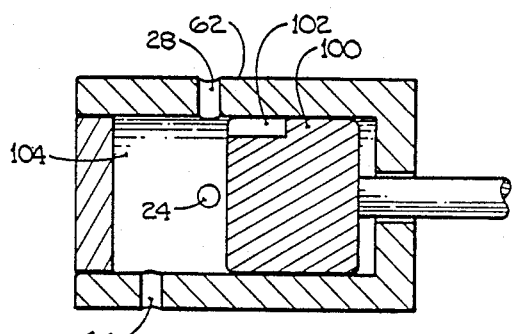

When valve 100 is longitudinally displaced in housing 62 to a second position as shown in FIG. 11B, all apertures in housing 62 are opened for fluid communication with chamber 104. Thus, first inlet 24, second inlet 28, outlet 36 and port 64 are all in mutual fluid communication. This, as will be appreciated by the skilled artisan, establishes a free-flow condition which allows the system to be purged of air.

With regard to all of the embodiments of the present invention, it is to be understood that either inlet 24 or inlet 28 may be used alone during the operation of pump 42. Thus, when not in use, first inlet 24 or second inlet 28 may be sealed in any manner known in the pertinent art.

Figure 13:
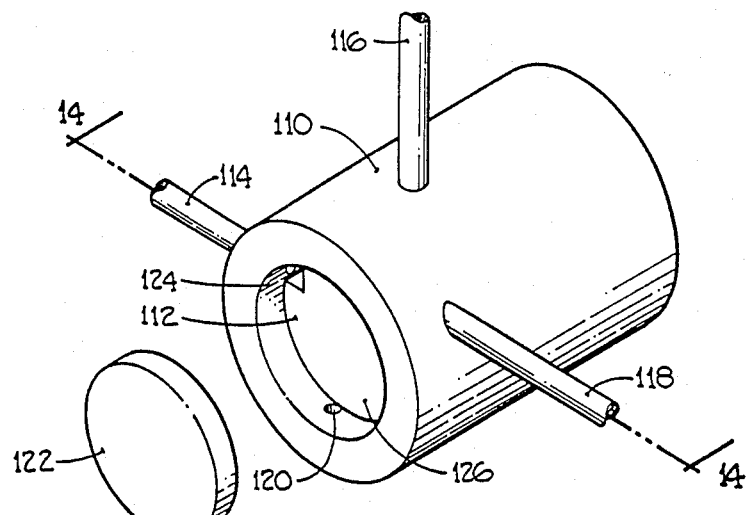
FIG. 13 is a partially exploded perspective view of an embodiment providing an off-set grooved valve of the present invention disposed in a housing.
Figure 14A:
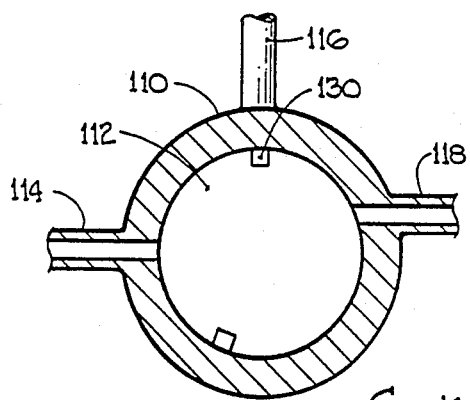
FIGS. 14A, B, C, and D are cross-sectional views of the off-set grooved valve in different orientations in the housing as seen along the line 14—14 in FIG. 13.

Still another embodiment of a valve for the present invention having off-set grooves is shown in FIG. 13 and FIGS. 14A, B, C and D. Referring initially to FIG. 13, it will be seen that a housing 110 is formed to receive a cylindrically shaped valve 112. Also, housing 110 is connectable in fluid communication with other structures through a first inlet 114, a second inlet 116, an outlet 118 and a port 120. As will be appreciated by reference to FIGS. 14A, B, C and D, first inlet 114 and outlet 118 are coplanar. On the other hand, as can, perhaps, be best seen by reference to FIG. 13, port 120 and second inlet 116 do not lie in this plane. Also, unlike other embodiments for the housing of the present invention, housing 110 does not have outlet 118 diametrically opposed to first inlet 114. Instead, there is an offset. This relationship is best seen in FIGS. 14A, B, C and D wherein it is shown that the arc distance between first inlet 114 and second inlet 116 is greater than the arc distance between second inlet 116 and outlet 118. Port 120, while not coplanar with second inlet 116, lies on a line diametrically opposed to second inlet 116.

FIG. 13 shows, in exploded perspective, a cap 122 which can be joined to rim 124 of housing 110 by any means well known in the art, such as by solvent bonding, to establish a fluid chamber 126. Fluid communication with chamber 126 is accomplished through apertures, such as the aperture 128 shown connecting inlet 114 in fluid communication with chamber 126. While port 120 is in continuous fluid communication with chamber 126, whether chamber 126 is in fluid communication with first inlet 114, second inlet 116 or outlet 118 depends on the position of valve 112 in housing 110.

Referring now to FIGS. 14A, B, C and D, valve 112 is seen as being formed with grooves 130 and 132 which are notched into valve 112 on its end which partially defines chamber 126. Importantly, grooves 130 and 132 are not diametrically opposed. Rather, their orientation on valve 112 is off-set and is determined by the arc relationship between first inlet 114 and outlet 118. This will be best appreciated by reference to FIG. 14D where it can be seen that when groove 132 is aligned with first inlet 114, groove 130 is aligned with outlet 118. An aside, it is noted here that this configuration establishes the direct free-flow path between inlet 114 and outlet 118 needed to remove air from the system.

Figure 14B:
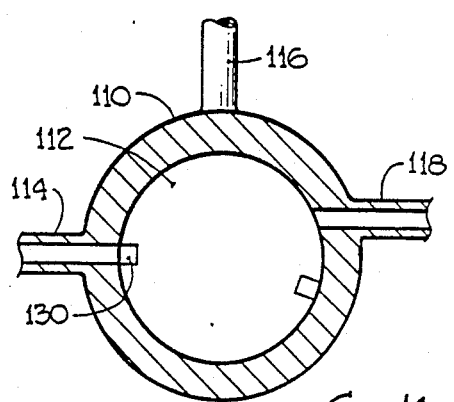
Figure 14C:
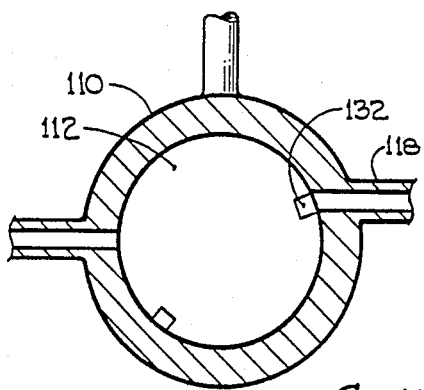
Figure 14D:
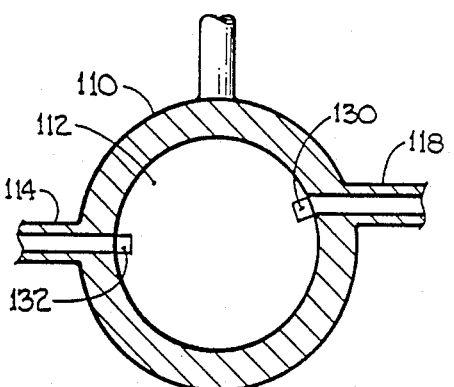

FIG. 14A shows a configuration for valve 112 in housing 110 which causes valve 112 to block first inlet 114 and outlet 118. Groove 130, however, is aligned with second inlet 116. Thus, there is fluid communication between whatever fluid source is attached to second inlet 116 and chamber 126. Since port 120 is in constant fluid communication with chamber 126, it follows that the fluid source connected to second inlet 116 is in fluid communication with pump chamber 32. Accordingly, pump 42 can draw fluid from this source (not shown) into pump chamber 32. Likewise, FIG. 14B shows a configuration in which valve 112 blocks second inlet 116 and outlet 118, but which aligns groove 130 with first inlet 114. This allows pump 42 to draw fluid from a fluid source (not shown) which is attached to first inlet 114. FIG. 14C shows a further rotation of valve 112 within housing 110 to align groove 132 with outlet 118. This, of course, also blocks fluid communication between first inlet 114 and second inlet 116 and chamber 126. Thus, with valve 112 oriented as shown in FIG. 14C, fluid communication is established between port 120 and outlet 118 through chamber 126.

In accordance with the above disclosure for various embodiments of the present invention, selective operation of valve 52, valve 88, valve 100 or valve 112, through the repective connection of each with pump 42, can allow pumping cycles which draw fluid into a pumping chamber through a first inlet alone or in sequential combination with the intake of fluids through a second inlet. Thus, the present invention allows for the pumping of precise volumes and concentrations of either mixed or unmixed solutions to patient 40. Further, each embodiment of the present invention provides for a free-flow configuration.

In its operation, cassette 20 of the present invention is engaged with pump 42 in a manner which brings connector 48 into engagement with shuttle 50. Stepper motor 56 drives shuttle 50 and piston 34 in a coordinated movement with the rotation of the particular valve body to provide for the intake of fluid from first inlet 24 into pump chamber 32 and the pumping of fluid from pump chamber 32 through outlet 36 to patient 40.

For an alternate embodiment of the present invention, longitudinal movement of valve body 100 within housing 62 can be accomplished to move valve 100 with respect to first inlet 24, outlet 36, and pump port 64 to allow for the simultaneous flow of fluid between first inlet 24, second inlet 28, outlet 36, and pump port 64. Valve 100 is subsequently repositionable within housing 62 to permit further normal pumping operation of the cassette 20 in conjunction with the pump 42.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A cassette for use with an I.V. infusion pump which comprises:

a housing forming a chamber having a first inlet, a second inlet, an outlet, and a port; and a cylindrical valve body having a first end and a second end and formed with a first groove and a second groove at the edge of said first end for respective simultaneous alignment with said first inlet and said outlet, said valve body being disposed in said chamber of said housing to permit continuous fluid communication between said port and said chamber and selectively block said first inlet, said second inlet or said outlet to establish fluid communication through said chamber from said first inlet to said port, from said second inlet to said port, from said port to said outlet, or from said first inlet to said outlet.

2. A cassette as recited in claim 1 wherein said first end is formed with a plurality of peripheral grooves, each appropriately alignable with said first inlet, said second inlet, said outlet and said port to establish fluid communication therebetween with said chamber.

3. A cassette as recited in claim 2 wherein a first and a second groove are diametrically opposed to establish a first fluid passageway through said chamber and a third and a fourth groove establish a second fluid passageway through said chamber.

4. A cassette as recited in claim 3 wherein said valve is rotationally disposed on said housing to separately establish fluid communication from said first inlet to said port or from said port to said outlet through said second fluid passageway and from said second inlet to said port or from said first inlet to said outlet through said first fluid passageway.

5. A cassette as recited in claim 1 wherein said housing is formed with a chamber and said valve is cylindrically shaped with a first end and a second end and said valve is slidably disposed in said chamber for rotation relative thereto and for longitudinal movement between a first position and a second position.

6. A cassette as recited in claim 5 wherein said first end is formed with a groove, said groove being alignable with either said first inlet, said second inlet or said outlet when said valve is in said first position to selectively establish fluid communication with said port.

7. A cassette as recited in claim 6 wherein movement of said valve into said second position blocks fluid communication with said second inlet and establishes direct fluid communication between said first inlet and said outlet.

8. A cassette as recited in claim 1 wherein said valve is formed with a first passageway to establish fluid communication between said first inlet and said port, a second passageway to selectively establish fluid communication between said second inlet and said port or between said first inlet and said outlet, and a third passageway to establish fluid communication between said port and said outlet.

9. A cassette as recited in claim 8 wherein said first, second and third passageways are substantially coplanar and parallel to each other.

10. A cassette as recited in claim 9 wherein said second passageway has an end formed as a recess having a first portion alignable for fluid communication with said first inlet and a second portion alignable for fluid communication with said second inlet.

11. A cassette as recited in claim 10 wherein said first portion is intermediate said second portion and said second passageway.

12. A cassette as recited in claim 1 wherein said housing is shaped as a hollow cylinder and said first inlet and said outlet lie in a plane which is substantially perpendicular to the longitudinal axis of said housing.

13. A cassette as recited in claim 12 wherein said first inlet is not diametrically opposed to said outlet.

14. A cassette for use with an I.V. infusion pump which comprises:
a housing formed with a fluid chamber and having a first inlet, a second inlet, an outlet, and a port; and
a valve body having a first end and a second end and formed with a first groove and a second groove at the edge of said first end for respective simultaneous alignment with said first inlet and said outlet, said valve body being disposed in said chamber of said housing to establish continuous fluid communication between said port and said chamber and being selectively positioned in said chamber to alternatively establish fluid communication between said chamber and either said first inlet, said second inlet, or said outlet, or to directly establish simultaneous fluid communication between said first inlet and said outlet through said chamber.

15. A cassette as recited in claim 14 wherein a first and a second notch are diametrically opposed to establish a first fluid passageway through said chamber and a third and a fourth groove establish a second fluid passageway through said chamber.

16. A cassette as recited in claim 15 wherein said valve is rotationally moveable on said housing to separately establish fluid communication from said first inlet to said port or from said port to said outlet through said second fluid passageway and from said second inlet to said port or from said first inlet to said outlet through said first fluid passageway.

17. A cassette for use with an IV infusion pump which comprises:
a housing formed with a chamber and having a first inlet, a second inlet, an outlet and a port for fluid communication with said chamber;
a valve body having a first end and a second end and formed with a first groove and a second groove at the edge of said first end for respective simultaneous alignment with said first inlet and said outlet, said valve body being disposed in said chamber and rotatable therein to selectively block fluid communication between said chamber and either both said second inlet and said outlet, or both said first inlet and said outlet, or both said first inlet and said second inlet, or said second inlet alone.

18. A cassete as recited in claim 17 wherein said housing is shaped as a hollow cylinder and said first inlet and said outlet lie in a plane which is substantially perpendicular to the longitudinal axis of said housing.

19. A cassette as recited in claim 18 wherein said first inlet is not diametrically opposed to said outlet.

* * * * *